United States Patent
Li et al.

(10) Patent No.: US 11,660,472 B2
(45) Date of Patent: May 30, 2023

(54) RADIOTHERAPY APPARATUS AND METHOD FOR DETERMINING TARGET POSITIONS USING RADIOTHERAPY APPARATUS

(71) Applicant: SHENZHEN OUR NEW MEDICAL TECHNOLOGIES DEVELOPMENT CO., LTD., Guangdong (CN)

(72) Inventors: Jiuliang Li, Guangdong (CN); Hao Yan, Guangdong (CN); Jinsheng Li, Guangdong (CN)

(73) Assignee: SHENZHEN OUR NEW MEDICAL TECHNOLOGIES DEVELOPMENT CO., LTD., Shenzhen (CN)

( * ) Notice: Subject to any disclaimer, the term of this patent is extended or adjusted under 35 U.S.C. 154(b) by 432 days.

(21) Appl. No.: 16/621,187

(22) PCT Filed: Jun. 19, 2017

(86) PCT No.: PCT/CN2017/089001
§ 371 (c)(1),
(2) Date: Dec. 10, 2019

(87) PCT Pub. No.: WO2018/232566
PCT Pub. Date: Dec. 27, 2018

(65) Prior Publication Data
US 2020/0108277 A1 Apr. 9, 2020

(51) Int. Cl.
*A61N 5/10* (2006.01)
(52) U.S. Cl.
CPC ......... *A61N 5/1049* (2013.01); *A61N 5/1037* (2013.01); *A61N 5/1067* (2013.01);
(Continued)

(58) Field of Classification Search
CPC ............ A61B 2034/2065; A61B 5/113; A61B 5/1135; A61B 5/7285; A61B 6/00;
(Continued)

(56) References Cited

U.S. PATENT DOCUMENTS

2005/0228263 A1 10/2005 Schwieker et al.
2006/0058637 A1* 3/2006 Sommer .............. A61N 5/1049
600/411
(Continued)

FOREIGN PATENT DOCUMENTS

CN        1668251 A      9/2005
CN     103083023 A      5/2013
(Continued)

OTHER PUBLICATIONS

International Search Report and Written Opinion for Application No. PCT/CN2017/089001, dated Mar. 21, 2018.

*Primary Examiner* — Thaddeus B Cox
*Assistant Examiner* — Marc D. Honrath
(74) *Attorney, Agent, or Firm* — Marshall, Gerstein & Borun LLP

(57) ABSTRACT

The present invention relates to a radiotherapy apparatus and a method for determining target positions using a radiotherapy apparatus, so as to accurately detect the motion of the tumor position. The method includes: a ray source locating in a first position, and emitting a radiation beam; a detector receiving the radiation beam emitted by the ray source at the first position, and generating first image data of the target according to the radiation beam emitted by the ray source at the first position; the ray source moving to a second position and emitting a radiation beam, wherein an interval at which the ray source moves from the first position to the second position is a positive integer multiple of a preset breathing cycle of a patient; the detector receiving the radiation beam emitted by the ray source at the second (Continued)

position, and generating second image data of the target according to the radiation beam emitted by the ray source at the second position; and determining position information of the target according to the first image data and the second image data.

17 Claims, 9 Drawing Sheets

(52) U.S. Cl.
CPC ......... *A61N 5/1068* (2013.01); *A61N 5/1081* (2013.01); *A61N 2005/1061* (2013.01)

(58) Field of Classification Search
CPC .................. A61B 6/4085; A61B 6/541; A61N 2005/1054; A61N 2005/1061; A61N 5/10; A61N 5/1037; A61N 5/1048; A61N 5/1049; A61N 5/1064; A61N 5/1067; A61N 5/1068; A61N 5/1077; A61N 5/1081; G06T 11/003; G06T 2207/10116; G06T 2207/10124; G06T 7/73

See application file for complete search history.

(56) References Cited

U.S. PATENT DOCUMENTS

| | | |
|---|---|---|
| 2011/0084211 A1 | 4/2011 | Yamaya et al. |
| 2012/0035462 A1* | 2/2012 | Maurer, Jr. .......... A61N 5/1077 600/411 |
| 2014/0050297 A1* | 2/2014 | Mostafavi .............. A61B 6/486 378/8 |
| 2014/0066749 A1* | 3/2014 | Dickerson ............ A61B 5/4836 600/413 |

FOREIGN PATENT DOCUMENTS

| | | |
|---|---|---|
| CN | 106310528 A | 1/2017 |
| CN | 106714905 A | 5/2017 |

* cited by examiner

RADIOTHERAPY APPARATUS AND METHOD FOR DETERMINING TARGET POSITIONS USING RADIOTHERAPY APPARATUS

CROSS-REFERENCE TO RELATED APPLICATION

This application is a national phase entry under 35 USC 371 of International Patent Application No. PCT/CN2017/089001 filed on 19 Jun. 2017, which is incorporated herein by reference in its entirety.

TECHNICAL HELD

The present disclosure relates to the field of radiotherapy instrument, and more particularly, to a radiotherapy apparatus and a method for determining target positions using the radiotherapy apparatus.

BACKGROUND

One of the key factors in radiation therapy is to maintain precise positioning of tumors during treatment. For example, lung tumors move with breathing, therefore it is very difficult to precisely position the tumors at each moment. Real-time tracking of the tumors becomes a challenging problem. In the existing methods, one method is to monitor external replacement signals associated with breathing, and based on this, the motion of the tumors is predicted. The external replacement signals include an up and down movement of markers on the patient's body surface, an increase or decrease of the amount of gas breathed by the patient, or a change of the patient's abdominal pressure. However, the external replacement signals cannot accurately characterize the motion of the tumors, and there is a large uncertainty. In addition, there have been many studies showing that there is a phase shift between the position of the tumors predicted by using the external replacement signals and the actual position of the tumors, and an amplitude of the shift varies with the patient's breathing, and is unpredictable and difficult to eliminate. Another method is to perform fluoroscopic imaging for the tumor region directly, and a 3D position of the tumor in space can be calculated through 2D positions of the tumor in two X-ray projections at an angle with each other.

A contrast of the tumor in the fluoroscopic image is low, so in most cases, the position of the tumor cannot be directly observed in the fluoroscopic image. To enhance the contrast of the fluoroscopic image, a plurality of metal markers (gold markers) are generally implanted into the tumor prior to imaging. The implantation of the gold markers not only brings additional surgical pain to the patient, but also may induce symptoms such as "pneumothorax". In addition, the gold markers themselves may move relative to the rumors over time, which brings higher error to the determination of the rumor position. However, if the gold markers are not implanted, limited visibility of the detected imaging may result in extremely low accuracy of tumor tracking. The above methods cannot accurately realize the real-time tracking of the tumor position during treatment in clinical application. Therefore, when developing a treatment plan, the doctor has to allocate prescription dose of radiation to an enlarged irradiation region covering a motion range of the tumor, so as to ensure that the tumor is always within the irradiation range during treatment. But this method causes insufficient irradiation to the tumor itself, and causes an additional irradiation to normal organs around the tumor, thereby causing damage to the normal organs around the tumor.

Therefore, how to accurately detect motion of the tumor position has become an urgent problem to be solved in the field.

SUMMARY

An objective of the present disclosure is to provide a radiotherapy apparatus and a method for determining target positions using a radiotherapy apparatus, so as to more accurately detect the position of tumors.

The above objective of the disclosure is achieved by the following technical solution.

Some embodiments of the present disclosure provide a method for determining target positions using a radiotherapy device, and the method includes:

a ray source locating at a first position, and emitting a radiation beam; a detector receiving the radiation beam emitted by the ray source at the first position, and generating first image data of a target according to the radiation beam emitted by the ray source at the first position; the ray source moving to a second position, and emitting a radiation beam, wherein an interval at which the ray source moves from the first position to the second position is a positive integer multiple of a preset breathing cycle of a patient; the detector receiving the radiation beam emitted by the ray source at the second position, and generating second image data of the target according to the radiation beam emitted by the ray source at the second position; and determining position information of the target according to the first image data and the second image data.

Some other embodiments of the present disclosure provide a method for determining target positions using a radiotherapy apparatus, and the method includes:

a ray source locating at a first position, and emitting a radiation beam; a detector receiving the radiation beam emitted by the ray source at the first position, and generating first image data of the target according to the radiation beam emitted by the ray source at the first position; the ray source moving to a second position, and emitting a radiation beam; the detector receiving the radiation beam emitted by the ray source at the second position, and generating second image data of the target according to the radiation beam emitted by the ray source at the second position; and determining position information of the target according to the first image data and the second image data; wherein an interval between the detector generating the first image data and the second image data is a positive integer multiple of a preset breathing cycle of a patient.

Some embodiments of the present disclosure provide a radiotherapy apparatus, the radiotherapy apparatus includes a computer device, a ray source and a detector receiving radiation beams emitted by the ray source, wherein, the computer device is configured to: control the ray source to locate at a first position, and to emit a radiation beam; control the detector to receive the radiation beam emitted by the ray source at the first position, and to generate first image data of a target according to the radiation beam emitted by the ray source at the first position; control the ray source to move to a second position and to emit a radiation beam; control the detector to receive the radiation beam emitted by the ray source at the second position, and to generate second image data of the target according to the radiation beam emitted by the ray source at the second position; and determine position information of the target according to the first image data and the second image data generated by the first controller; wherein an interval at which the ray source moves from the first position to the second position is a positive integer multiple of a preset breathing cycle of a patient; and/or an interval between the detector generating the first image data and the second image data is a positive integer multiple of a preset breathing cycle of a patient.

In above way, the detector receives the radiation beam emitted by the ray source at the first position to generate the first image data, and then the detector receives the radiation beam emitted by the ray source at the second position to generate the second image data. Since the interval at which the ray source moves from the first position to the second position is the positive integer multiple of the breathing cycle of the patient, the first image data and the second image data that are acquired are image data of a same node in different breathing cycles of the patient, thereby avoiding the problem of inaccurate tumor imaging caused by time delay, and then providing more accurate position information of the target for radiotherapy, and avoiding damage caused by additional irradiation to normal organs around the target during radiotherapy.

DETAILED DESCRIPTION

Although the flow diagrams describe the operations as sequential processing, many of the operations can be implemented in parallel, concurrently or simultaneously. The order of each operation can be rearranged. The processing may be terminated after completing the operations but the processing may still include additional steps not included in the figures. The processing can correspond to methods, functions, procedures, subroutines, subprograms, and the like.

Computer device includes user device and network device. The user device or the client includes, but is not limited to, computer, smart phone, PDA, etc. The network device includes, but is not limited to, single network server, server group composed of a plurality of network servers, or cloud composed of a large number of computers or network servers based on cloud computing. The computer device can be operated alone to carry out the present disclosure, and can also access the network and carry out the present disclosure by interactive operating with other computer devices in the network. The network in which the computer device is located includes, but is not limited to, Internet, wide area network, metropolitan area network, local area network, VPN network, etc.

The terms "first", "second" and the like may be used herein to describe each unit, but the units should not be limited by these terms, and the terms are used only to distinguish one unit from another. The term "and/or" used herein includes any and all combinations of one or more of the associated items listed. When a unit is "connected" or "coupled" to another unit, it can be directly connected or coupled to another unit, or an intermediate unit may be existed.

The terms used herein are only intended to describe the specific embodiments, but are not intended to limit exemplary embodiments. The singular forms "one" and "a/an" used herein are also intended to include the plural, unless the context clearly indicates otherwise. It will also be understood that the terms "include" and/or "comprise" used herein mean the existence of the stated features, integers, steps, operations, units and/or components, and do not exclude the existence or addition of one or more another features, integers, steps, operations, units, components and/or combinations thereof.

The present disclosure will be further described below in combination with the drawings and preferred embodiments.

Figure 1:
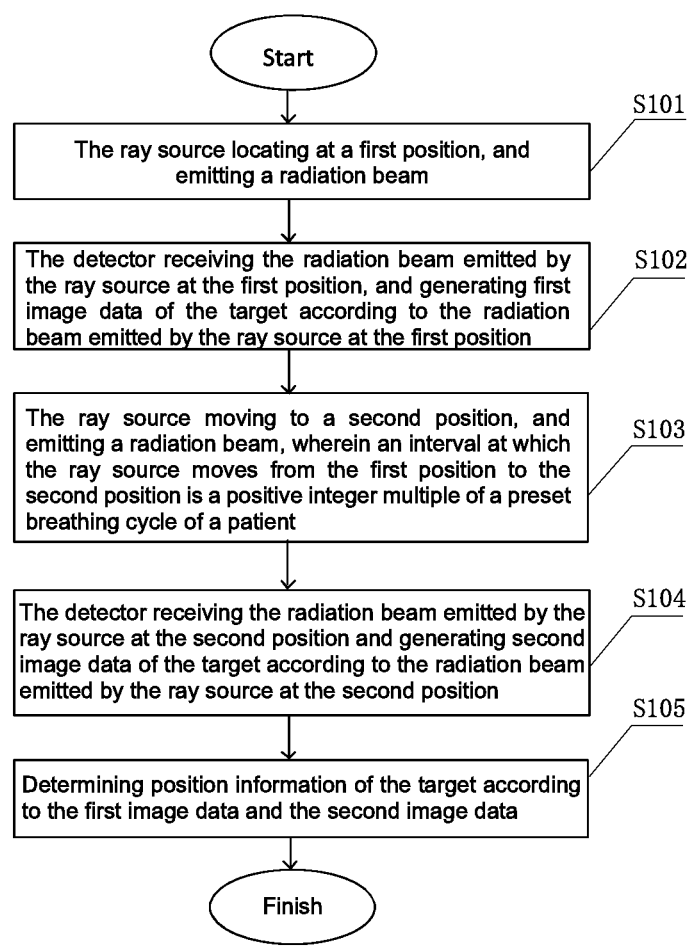
FIG. 1 is a flow diagram of a method for determining target positions using a radiotherapy apparatus according to some embodiments of the present disclosure.

As shown in FIG. 1, some embodiments of the present disclosure provide a method for determining target positions using a radiotherapy apparatus, the radiotherapy apparatus includes a ray source and a detector receiving radiation beams emitted by the ray source, and the method includes:

S101: the ray source locating at a first position, and emitting a radiation beam;

S102: the detector receiving the radiation beam emitted by the ray source at the first position, and generating first image data of the target according to the radiation beam emitted by the ray source at the first position;

S103: the ray source moving to a second position, and emitting a radiation beam, wherein an interval at which the ray source moves from the first position to the second position is a positive integer multiple of a preset breathing cycle of a patient;

S104: the detector receiving the radiation beam emitted by the ray source at the second position, and generating second image data of the target according to the radiation beam emitted by the ray source at the second position; and S105: determining position information of the target according to the first image data and the second image data.

In the embodiments of the present disclosure, the interval at which the ray source moves from the first position to the second position is the positive integer multiple of the preset breathing cycle of the patient, that is, an interval between the detector generating the first image data and the second image data is the positive integer multiple of the preset breathing cycle of the patient.

In this way, the detector receives the radiation beam emitted by the ray source at the first position to generate the first image data, and then the detector receives the radiation beam emitted by the ray source at the second position to generate the second image data. Since the interval at which the ray source moves from the first position to the second position is the positive integer multiple of the breathing cycle of the patient, the first image data and the second image data that are acquired are image data of a same node in different preset breathing cycles of the patient, thereby avoiding the problem of inaccurate tumor imaging caused by time delay, and then providing more accurate position information of the target for radiotherapy, and avoiding damage caused by additional irradiation to normal organs around the target during radiotherapy.

In the present embodiment, the breathing cycle includes three parts: inhalation, exhalation, and breath-holding. Wherein, the inhalation is an active activity of inhaling air, so that the lungs are filled with pure, fresh air. The exhalation is a passive action of breathing to breathe out stale air and empty the lungs. The breath-holding refers to a normal pause between the inhalation and exhalation, and the breath-holding is divided into two parts, which include breath-holding after inhalation and breath-holding after exhalation. The breathing cycle of the patient is to complete the above three parts, that is, the breathing cycle of the patient is a time taken to complete the whole process of inhalation, exhalation, and breath-holding. For example, in general, the time required for a human to complete a breathing cycle is approximately 3 to 4 seconds. However, the breathing cycle may change under special circumstances or pathological conditions. In the present embodiments, an initial breathing cycle of the patient can be obtained by performing a breathing training for the patient, or the breathing cycle of the patient can be also obtained by other means, such as, using a breathing monitoring device.

In some embodiments of the present disclosure, the preset breathing cycle is a breathing cycle set by an initially input of the system, and the preset breathing cycle may be an average breathing cycle of the patient, or may also be a breathing cycle of the patient obtained by performing a training for the patient by the therapist.

In the embodiments of the present disclosure, the interval at which the ray source moves from the first position to the second position may be one, two or three times and the like of the preset breathing cycle.

In the embodiments of the present disclosure, a fixing mode and a motion mode of the ray source are not specifically limited, as long as the ray source can be controlled to move from the first position to the second position. For example, the ray source may be mounted on a cantilever, or a C-arm, or a ring frame, or a roller, etc. In the embodiments of the present disclosure, the manner in which the detector receives the radiation beam and the number of detectors are also not specifically limited. The detector can move relative to the ray source. For example, when the ray source moves to the first position, the detector moves to a position opposite to the first position, so as to receive the radiation beam; when the ray source moves to the second position, the detector moves to a position opposite to the second position, so as to receive the radiation beam. Of course, it is also possible to provide two detectors, wherein one receives the radiation beam emitted by the ray source at the first position and the other receives the radiation beam emitted by the ray source at the second position. That is, the number of detectors is not specifically limited in the present disclosure, and the number of detectors may be set to one, two, three or more. In the embodiments of the present disclosure, the ray source may be a ray source that emits KV-level rays, or may be a ray source that emits MV-level or other levels, etc.

Figure 2:
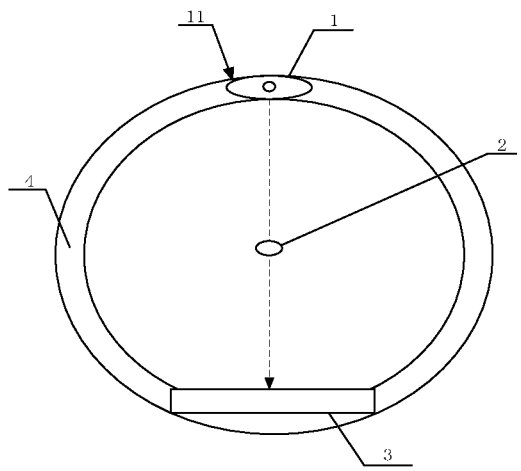
FIG. 2 is a schematic diagram of a ray source at a first position according to some embodiments of the present disclosure.
Figure 3:
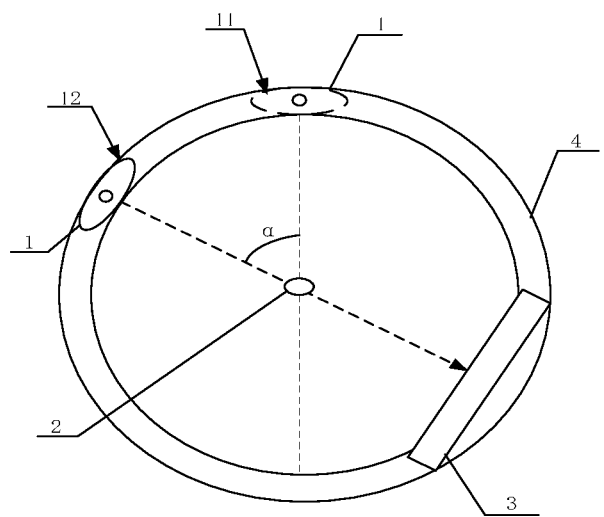
FIG. 3 is a schematic diagram of the ray source at a second position according to some embodiments of the present disclosure.
Figure 4:
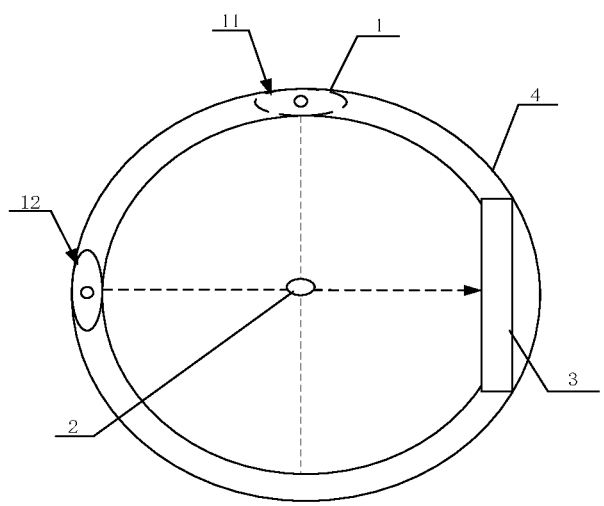
FIG. 4 is a schematic diagram of the ray source at another second position according to some embodiments of the present disclosure.

As shown in FIG. 2, the present embodiment is illustrated by taking a roller as an example. The ray source 1 and the detector 3 are mounted on the roller 4. A radiation beam emitted by the ray source 1 passes through the target 2, and the detector 3 receives the radiation beam passing through the target 2, and acquires image data therefrom. As shown in FIGS. 2 and 3, in this embodiment, taking the detector moving relative to the ray source as an example for exemplary illustration. The detector 3 moves relative to the ray source 1, when the ray source 1 locates at the first position 11, the detector 3 is opposite to the ray source 1 and receives the radiation beam of the ray source 1. As shown in FIG. 3, when the ray source 1 moves to the second position 12, the detector 3 moves to a position opposite to the ray source 1 and receives the radiation beam emitted by the ray source 1 at the second position 12. Wherein, An angle α between the first position 11 and the second position 12 may be range from 0° to 180°, for example, 0°, 45°, 90° or 180°, etc. When the angle α between the first position 11 and the second position 12 is 0°, the first position is overlapped with the second position after passing through a period of time that is the positive integer multiple of the breathing cycle of the patient. When the angle α between the first position 11 and the second position 12 may also be 180°, the first position is opposite to the second position after passing through the period of time that is the positive integer multiple of the breathing cycle of the patient. The angle α between the first position 11 and the second position 12 may also be other angles, such as 90°. As shown in FIG. 4, when the angle α is 90°, the ray source 1 at the first position 11 and the ray source at the second position 12 are an orthogonal relationship, and the target 2 displayed in the first image data that is acquired and the target 2 displayed in the second image data that is acquired are also an orthogonal relationship. In this way, position information of the target in a three-dimensional direction can be obtained through the image data acquired from two vertical angles, thereby determining precise position information of the target in the three-dimensional direction according to the first image data and the second image data, and then improving the accuracy of the position information of the target acquired, and providing more accurate position information of the target for radiotherapy. Of course, the angle α between the first position and the second position may also be other values, such as 10°, 25°, 30°, 31°, 35°, 45°, 50°, 60°, 66°, 79°, 88°, 92°, 100°, 120°, 140°, 155°, 176°, etc., which can be set according to actual needs.

In some embodiments of the present disclosure, the ray source 1 can be rotated circumferentially around the patient, and the method for determining the target positions in the embodiments of the present disclosure further includes: setting a rotation rate of the ray source. Wherein the rotation rate of the ray source is: $x=(\alpha/NT)$, wherein x is a rotational angular rate, α is the angle between the first position and the second position, T is the preset breathing cycle of the patient, and NT is the interval at which the ray source moves from the first position to the second position, and N is a positive integer.

Figure 5:
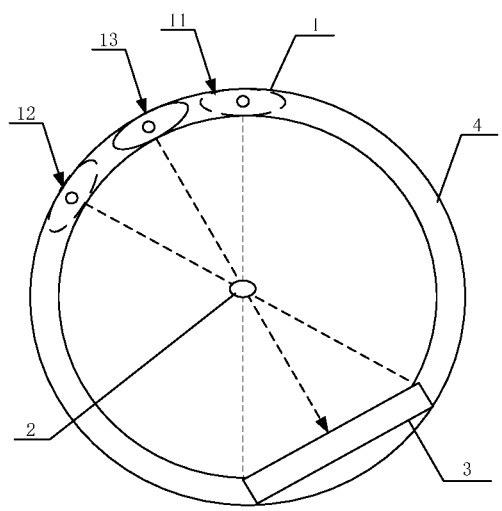
FIG. 5 is a schematic diagram of the ray source at a third position according to some embodiments of the present disclosure.
Figure 6:
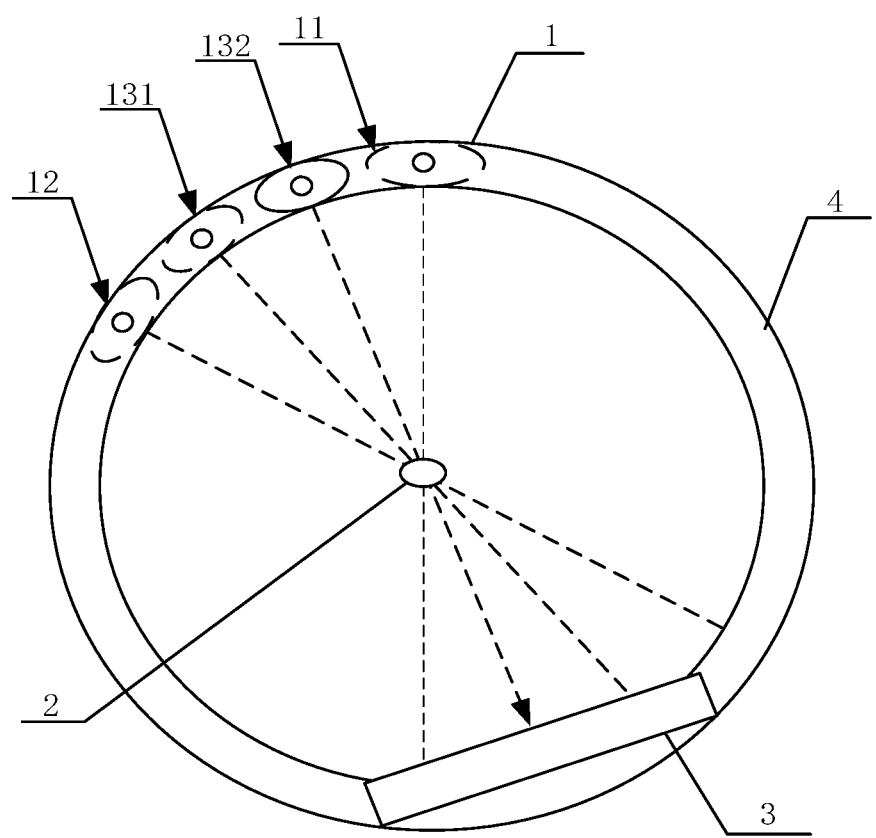
FIG. 6 is a schematic diagram of a third position according to some embodiments of the present disclosure.

In the embodiments of the present disclosure, the ray source is not limited to only move to the first position and the second position, and can also move to more other positions. For example, as shown in FIG. 5, in some embodiments of the present disclosure, the ray source 1 can also move to a third position 13. The third position 13 in FIG. 5 is only one example, and it may also locate at other positions on the circumference. In the embodiments of the present disclosure, the ray source can also move to a fourth position, a fifth position, and the like. In addition, the third position 13 can include two or more different circumferential positions. For example, as shown in FIG. 6, the third position includes a first third position 131 and a second third position 132, and then the changes of the position of the target that are acquired are more precise. It will be noted that, when the interval at which the ray source moves from the first position to the second position is one time of the preset breathing cycle of the patient, the third position may be a position corresponding to any time point within the breathing cycle. When the interval at which the ray source moves from the first position to the second position is many times of the preset breathing cycle of the patient, the third position may be a position corresponding to any time point within one breathing cycle, or may be a position corresponding to any time point within different breathing cycles.

Figure 7:
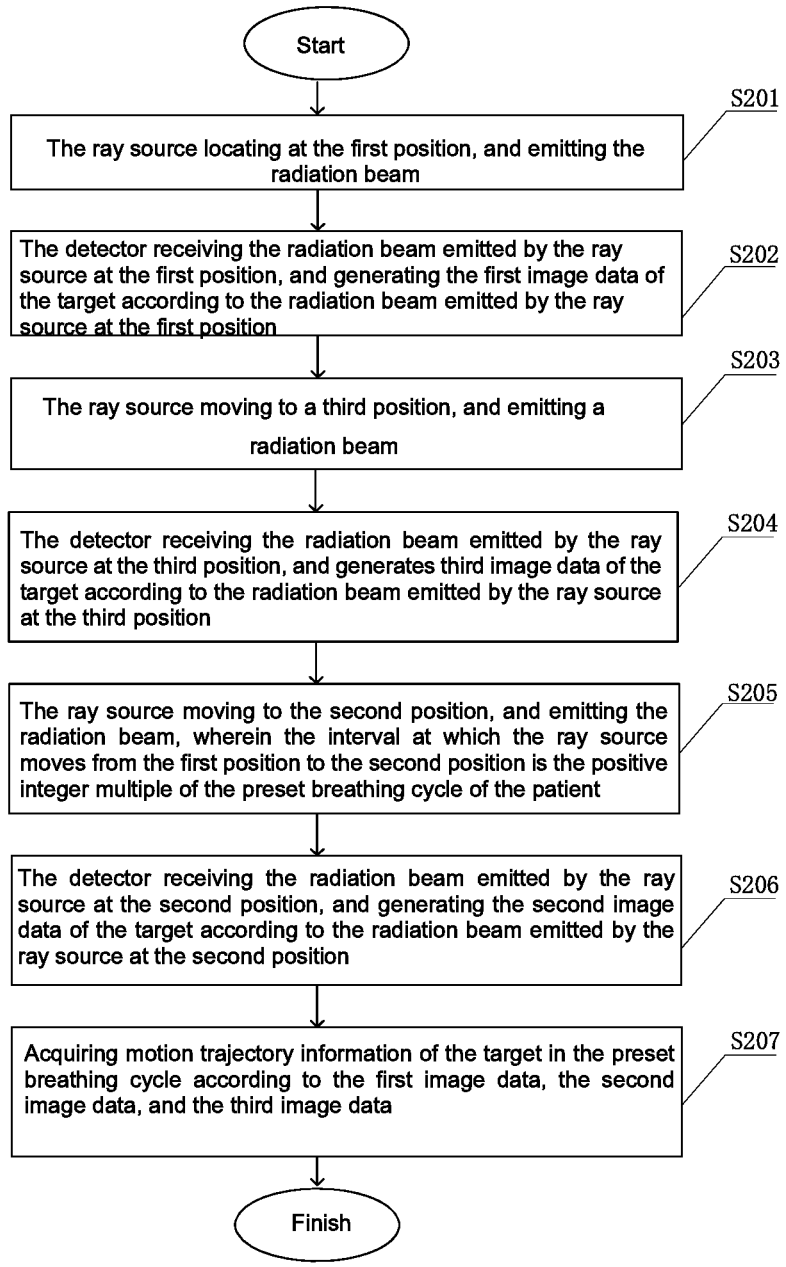
FIG. 7 is a flow diagram of a method for determining motion trajectory information of the target in a breathing cycle using a radiotherapy apparatus according to some embodiments of the present disclosure.

Some embodiments of the present disclosure provide the method for determining target positions using the radiotherapy apparatus. As shown in FIG. 5, before the ray source 1 moves to the second position 12, the ray source 1 moves to the third position 13 and emits a radiation beam. The detector 3 receives the radiation beam emitted by the ray source 1 at the third position 13 and generates third image data of the target according to the radiation beam emitted by the ray source 1 at the third position 13. Specifically, as shown in FIG. 7, the method includes:

S201: the ray source locating at the first position, and emitting the radiation beam;

S202: the detector receiving the radiation beam emitted by the ray source at the first position, and generating the first image data of the target according to the radiation beam emitted by the ray source at the first position;

S203: the ray source moving to the third position, and emitting the radiation beam;

S204: the detector receiving the radiation beam emitted by the ray source at the third position, and generating the third image data of the target according to the radiation beam emitted by the ray source at the third position;

S205: the ray source moving to the second position and emitting the radiation beam, wherein the interval at which the ray source moves from the first position to the second position is the positive integer multiple of the preset breathing cycle of the patient;

S206: the detector receiving the radiation beam emitted by the ray source at the second position, and generating the second image data of the target according to the radiation beam emitted by the ray source at the second position; and S207: acquiring motion trajectory information of the target in the preset breathing cycle according to the first image data, the second image data, and the third image data.

The ray source 1 moves from the first position 11 to the third position 13 and then to the second position 12, that is, the third position 13 can be any position between the first position 11 and the second position 12. For example, in a case where a time between the first position 11 and the second position 12 is exactly one preset breathing cycle, the first position 11, the second position 12, and the third position 13 are different positions of the ray source in a same preset breathing cycle, and the third position 13 is any position within the preset breathing cycle. In this way, the ray source 1 is controlled to move to the third position 13, and the detector 3 receives the radiation beam emitted by the ray source 1 at the third position 13, thereby generating the third image data. In this way, the motion trajectory information of the target 2 can be acquired in combination with the first image data, the second image data and the third image data, and the positions of the target 2 at different nodes in one preset breathing cycle can be obtained. Specifically, in addition, a current breathing cycle of the patient can also be acquired by using the method in this embodiment, for example, according to the comparison between the acquired image data and the previous image data, the changes of the node position of the previous breathing cycle are observed, thereby determining whether the breathing cycle has changed, and obtaining a specific value of the current breathing cycle of the patient. However, the third position 13 is not only limited to a position between the first position 11 and the second position 12, and may also locate at other positions, it is merely an exemplary illustration in this embodiment.

Exemplary, as shown in FIG. 6, the third position includes at least two different positions, such as, the first third position 131 and the second third position 132 in FIG. 6, wherein, the first third position 131 and the second third position 132 are both arranged between the first position 11 and the second position 12. However, in some embodiments of the present embodiments, the first third position 131 or the second third position 132 is arranged at a position other than a position between the first position 11 and the second position 12, for example, the first third position 131 is arranged at a position other than a position between the first position 11 and the second position 12, and the second third position 132 is arranged between the first position 11 and the second position 12. In some other embodiments of the present disclosure, the first third position 131 and the second third position 132 are both arranged at positions other than positions between the first position 11 and the second position 12. The detector generates at least two different third image data of the target at different positions respectively, and the motion trajectory information of the target in one breathing cycle is acquired according to the first image data, the second image data, and the at least two different third image data.

The third position may include more different positions, such as three different positions, or four different positions, or even more different positions. At least two different positions included in the third position may be randomly distributed. When the third position includes more than one, the positions of the target at a plurality of nodes in one preset breathing cycle can be acquired, so that the position changes of the target that are acquired are more accurate, thereby being able to obtain more detailed motion trajectory information of the target.

Figure 8:
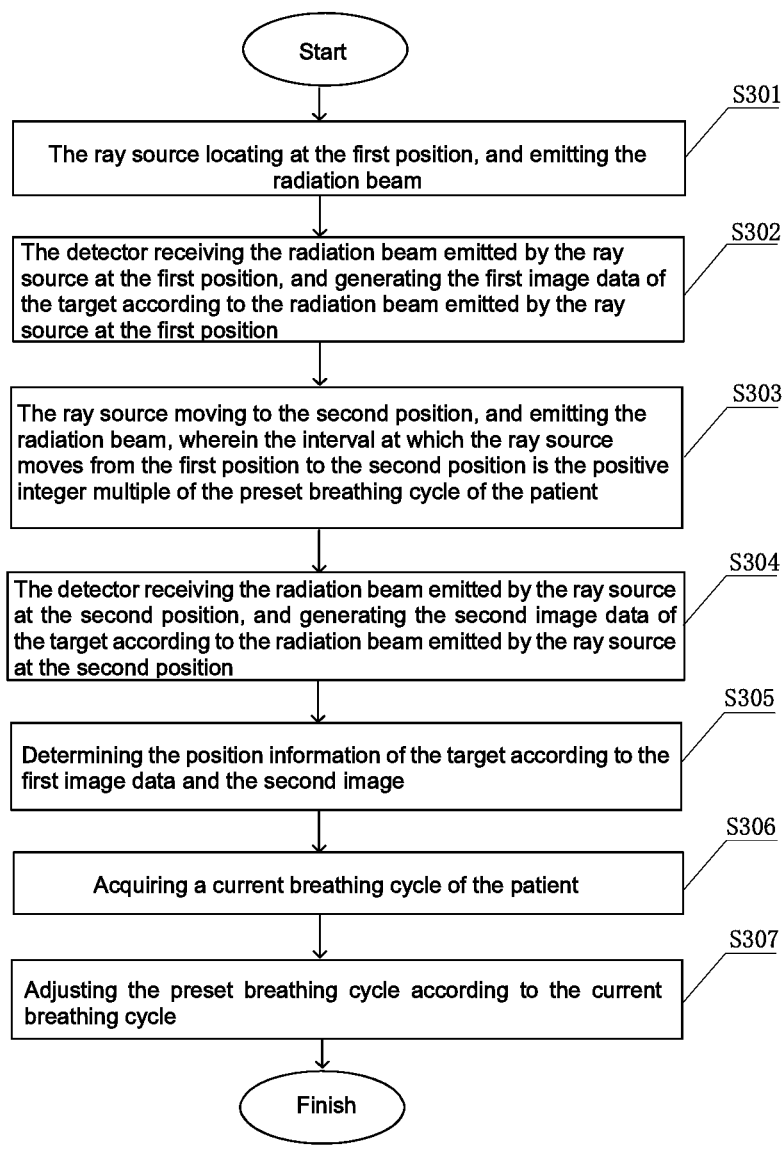
FIG. 8 is a flow diagram of another method for determining target positions using a radiotherapy apparatus according to some embodiments of the present disclosure.

Some embodiments of the present disclosure provide the method for determining target positions using the radiotherapy apparatus. Exemplary, as shown in FIG. 8, the method includes:

S301: the ray source locating at the first position, and emitting the radiation beam;

S302: the detector receiving the radiation beam emitted by the ray source at the first position, and generating the first image data of the target according to the radiation beam emitted by the ray source at the first position;

S303: the ray source moving to the second position and emitting the radiation beam, wherein the interval at which the ray source moves from the first position to the second position is the positive integer multiple of the preset breathing cycle of the patient;

S304: the detector receiving the radiation beam emitted by the ray source at the second position, and generating the second image data of the target according to the radiation beam emitted by the ray source at the second position;

S305: determining the position information of the target according to the first image data and the second image data;

S306: acquiring a current breathing cycle of the patient; and

S307: adjusting the preset breathing cycle according to the current breathing cycle.

The breathing cycle of the patient can be acquired through breathing training and the like before treatment, thereby the breathing cycle being used as the preset breathing cycle. When the patient is just starting treatment, the preset breathing cycle can be used to perform radiotherapy or imaging for the patient. In order to perform more precise treatment, the current breathing cycle of the patient can be acquired, so that it can be known whether the breathing cycle of the patient has changed. If a change has been occurred, the preset breathing cycle can be replaced by the current breathing cycle before the next breathing cycle starts. Of course, the steps of the specific method are not specifically limited in the present disclosure, and are only illustrated by taking the above steps as an example. For example, the above S306 and S307 may also be performed before S303, and the preset breathing cycle in S303 may be replaced with the current breathing cycle of the patient acquired.

Through acquiring the current breathing cycle of the patient and adjusting the preset breathing cycle, the breathing cycle is more accurate, thereby providing more accurate data for treatment. For example, if the breathing cycle of the patient acquired before treatment is 4 seconds, however, the current breathing cycle of the patient is 4.2 seconds, the preset breathing cycle of 4 seconds is changed to the current breathing cycle of 4.2 seconds in order to perform treatment more accurately. In some embodiments of the present disclosure, the current breathing cycle of the patient is acquired through performing breathing training for the patient in a current state. In some other embodiments of the present disclosure, the current breathing cycle is acquired through analyzing the acquired image data. In addition, other methods can also be used to acquire the current breathing cycle, and the specific method of acquiring the breathing cycle of the patient is not limited in the embodiment.

In the embodiments of the present disclosure, Exemplary, the current breathing cycle of the patient is acquired by the following method: the current breathing cycle of the target is acquired according to the first image data, the second image data, and the third image data. And then the preset breathing cycle is adjusted according to the current breathing cycle.

Through collecting the image data of the target, the motion trajectory of the target is acquired according to the image data, and then the breathing cycle is acquired according to the motion trajectory. The breathing cycle obtained by using this method is more precise in the breathing tracking. As described above, in this embodiment, the current breathing cycle of the patient is acquired by using this method, so that it can be known whether the breathing cycle of the patient has changed. If a change has been occurred, the preset breathing cycle is replaced with the current breathing cycle of the patient acquired, so that the breathing cycle is more accurate, thereby providing more accurate data for treatment. The method adopted in the embodiment can quickly acquire the current breathing cycle of the patient, and is convenient for implementation and use in treatment.

Figure 9:
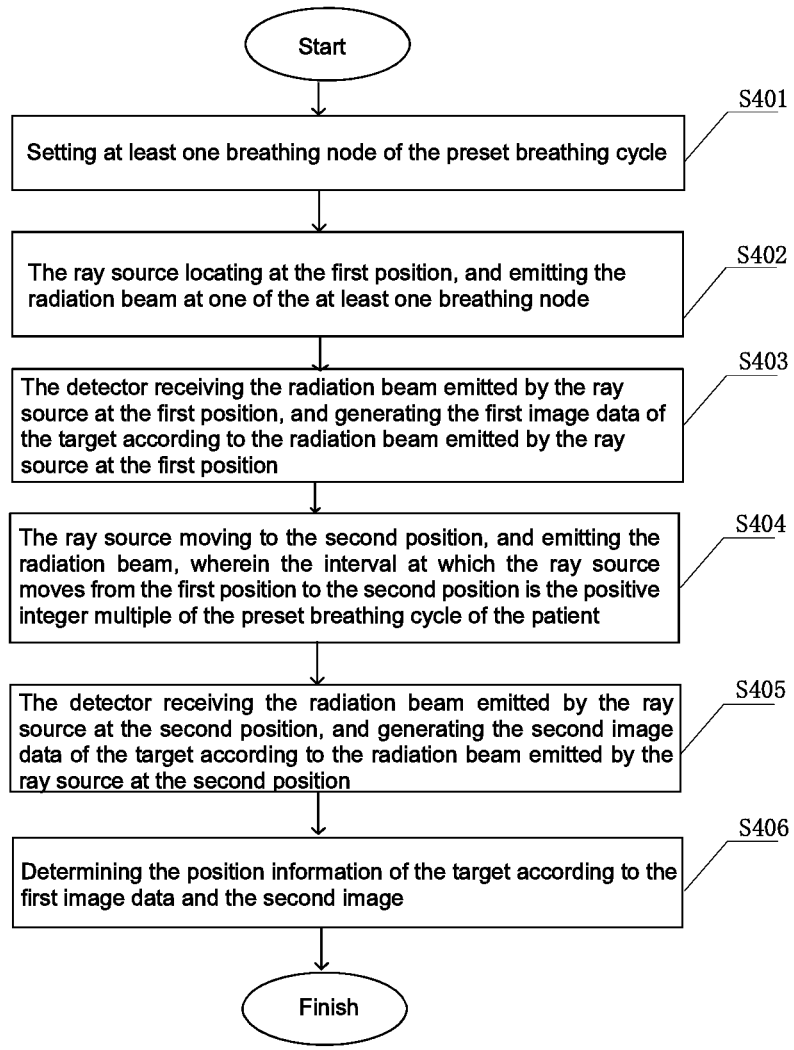
FIG. 9 is a flow diagram of yet another method for determining target positions using a radiotherapy apparatus according to some embodiments of the present disclosure.

Some embodiments of the present disclosure provide the method for determining target positions using the radiotherapy apparatus. Exemplary, as shown in FIG. 9, the method includes:

S401: setting at least one breathing node of the preset breathing cycle;

S402: the ray source locating at the first position, and emitting the radiation beam at one of the at least one breathing node;

S403: the detector receiving the radiation beam emitted by the ray source at the first position, and generating the first image data of the target according to the radiation beam emitted by the ray source at the first position;

S404: the ray source moving to the second position, and emitting the radiation beam, wherein the interval at which the ray source moves from the first position to the second position is the positive integer multiple of the preset breathing cycle of the patient;

S405: the detector receiving the radiation beam emitted by the ray source at the second position, and generating the second image data of the target according to the radiation beam emitted by the ray source at the second position; and S406: determining the position information of the target according to the first image data and the second image data.

In this way, the ray source can be controlled to emit the radiation beam at the preset breathing node, and after receiving the radiation beam, the detector acquires the image data, which can be compared with image data of other identical breathing nodes. In this way, the current state of the patient can be compared with a previous state at the same node to determine whether the breathing cycle of the patient has changed, and a specific value of breathing cycle change is specifically determined through a magnitude of position change, thereby acquiring the current breathing cycle of the patient. The previous preset breathing cycle can also be replaced with the current breathing cycle of the patient acquired after acquiring the current breathing cycle of the patient, so that the breathing cycle is more accurate, thereby providing more accurate data for treatment. Therefore, the current breathing cycle of the patient can also be acquired through the method of this embodiment, and thereby providing more accurate data for the treatment. The breathing node in the embodiment may be any node of the breathing cycle, such as T/5, T/4, T/2, 5T/8, 3T/4, 5T/6, and the like.

Some embodiments of the present disclosure provide the method for determining target positions using the radiotherapy apparatus, and the method includes: acquiring image data of a same breathing node in different preset breathing cycles; and determining the current breathing cycle of the patient according to the image data of the same breathing node in different preset breathing cycles.

Figure 10:
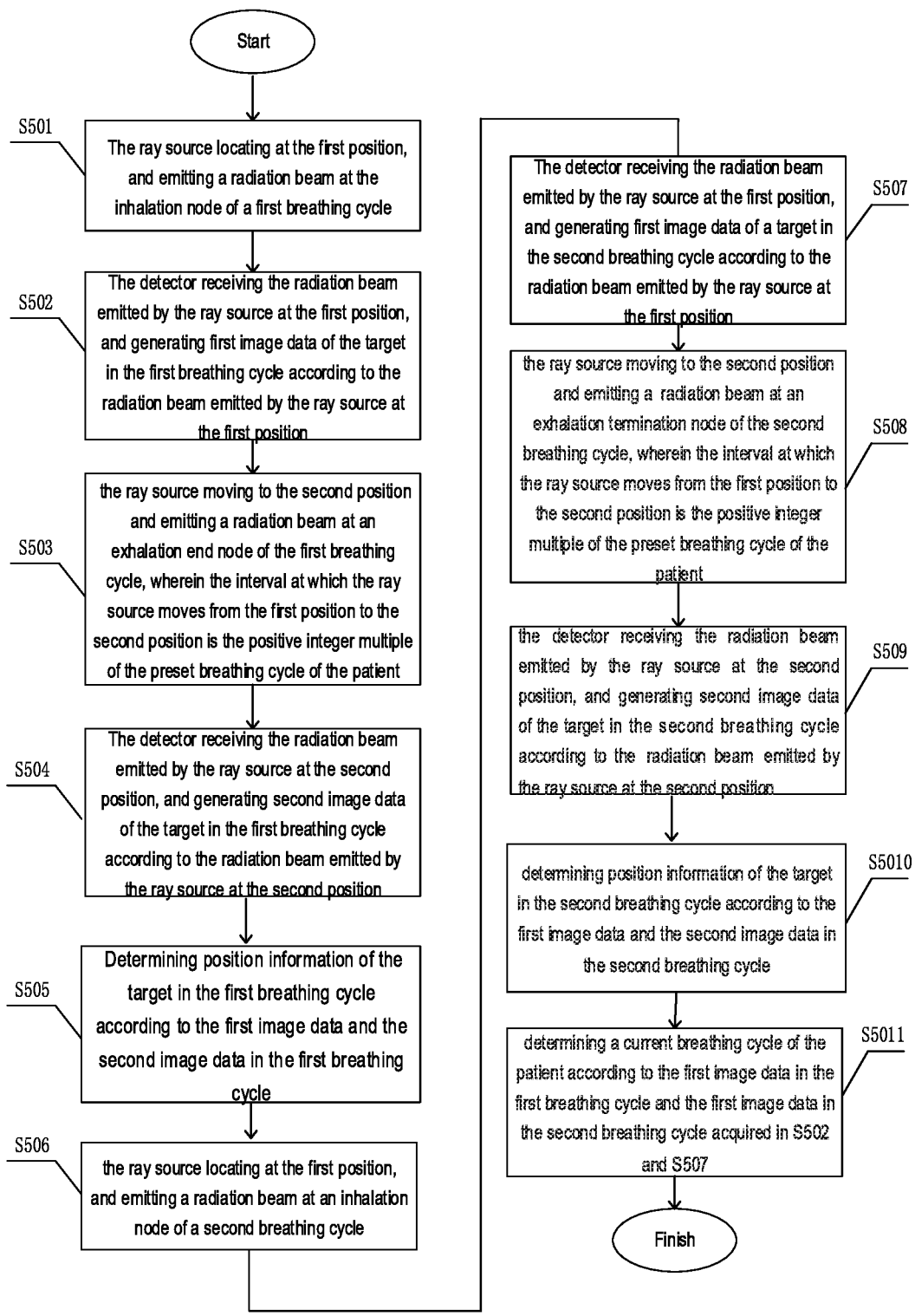
FIG. 10 is a flow diagram of still another method for determining target positions using a radiotherapy apparatus according to some embodiments of the present disclosure.

Exemplary, as shown in FIG. 10, taking the ray source locating at the first position at an inhalation node as an example, the method includes:

S501: the ray source locating at the first position, and emitting a radiation beam at the inhalation node of a first breathing cycle;

S502: the detector receiving the radiation beam emitted by the ray source at the first position, and generating first image data of the target in the first breathing cycle according to the radiation beam emitted by the ray source at the first position;

S503: the ray source moving to the second position and emitting a radiation beam at an exhalation termination node of the first breathing cycle, wherein the interval at which the ray source moves from the first position to the second position is the positive integer multiple of the preset breathing cycle of the patient, herein, exemplary one times; that is, the ray source moves from the first position to the second position in the first breathing cycle;

S504: the detector receiving the radiation beam emitted by the ray source at the second position, and generating second image data of the target in the first breathing cycle according to the radiation beam emitted by the ray source at the second position;

S505: determining position information of the target in the first breathing cycle according to the first image data in the first breathing cycle and the second image data in the first breathing cycle;

S506: the ray source locating at the first position and emitting a radiation beam at an inhalation node of a second breathing cycle;

S507: the detector receiving the radiation beam emitted by the ray source at the first position, and generating first image data of the target in the second breathing cycle according to the radiation beam emitted by the ray source at the first position;

S508: the ray source moving to the second position and emitting a radiation beam at an exhalation termination node of the second breathing cycle, wherein the interval at which the ray source moves from the first position to the second position is the positive integer multiple of the preset breathing cycle of the patient, herein, exemplary one times; that is, the ray source moves from the first position to the second position in the second breathing cycle;

S509: the detector receiving the radiation beam emitted by the ray source at the second position, and generating second image data of the target in the second breathing cycle according to the radiation beam emitted by the ray source at the second position;

S5010: determining position information of the target in the second breathing cycle according to the first image data in the second breathing cycle and the second image data in the second breathing cycle; and S5011: determining the current breathing cycle of the patient according to the first image data in the first breathing cycle and the first image data in the second breathing cycle acquired in S502 and S507.

Of course, S5011 may also be to determine the current breathing cycle of the patient according to the second image data in the first breathing cycle and the second image data in the second breathing cycle acquired in S504 and S509. The order of the above S5011 is not limited.

In above contents, take as an example the interval at which the ray source moves from the first position to the second position is the preset breathing cycle of the patient. Of course, the interval at which the ray source moves from the first position to the second position may also be many times of the preset breathing cycle of the patient, which can refer to the above embodiments, and will not be specifically described herein.

In this way, according to image data acquired from the same breathing node in different breathing cycles in the treatment process, the image data of the same breathing node in different breathing cycles can be compared with each other, thereby determining whether the breathing cycle of the patient has changed, and a magnitude of a change is obtained through the image data, thereby obtaining the current breathing cycle of the patient. Wherein different breathing cycles may be two adjacent breathing cycles, or three or more adjacent breathing cycles, or any two or three or more breathing cycles that are not adjacent to each other.

In some embodiments of the present disclosure, different breathing cycles is two adjacent breathing cycles, so that it is possible to know whether the breathing cycle of the patient has changed and a specific change situation in a short-term time. In some other embodiments of the present disclosure, different breathing cycles are three or more adjacent breathing cycles, so that more image data can be compared to acquire the change of the breathing cycle and a value of the current breathing cycle of the patient accurately. In some other embodiments of the present disclosure, different breathing cycles are any two breathing cycles that are not adjacent to each other, so that the breathing cycles of the patient in different time periods can be compared to acquire the breathing changes in different time periods, thereby providing more abundant data for treatment. In some other embodiments of the present disclosure, different breathing cycles are any three or more breathing cycles that are not adjacent to each other, and so more changes of the breathing cycles of the patient in different time periods can be acquired to more accurately know the changes of the patient's pathological state.

In this method of the present embodiment, through comparing the image data of the same breathing node in different breathing cycles in the treatment process, a change state of the breathing cycle can be acquired, and the value of the current breathing cycle of the patient can be acquired, so that the preset breathing cycle is adjusted according to the current breathing cycle acquired, thereby providing more accurate data for treatment. In this way, in the absence of the preset image data, the data of the current breathing cycle of the patient can be acquired by comparing the plurality of image data in the treatment, which facilitates the acquisition of the breathing cycle in the treatment.

Some embodiments of the present disclosure provide the method for determining target positions using the radiotherapy apparatus, the method further includes: acquiring preset image data of the target; determining first preset image data at the first position according to the preset image data; and adjusting the ray source according to the first image data and the first preset image data.

Figure 11:
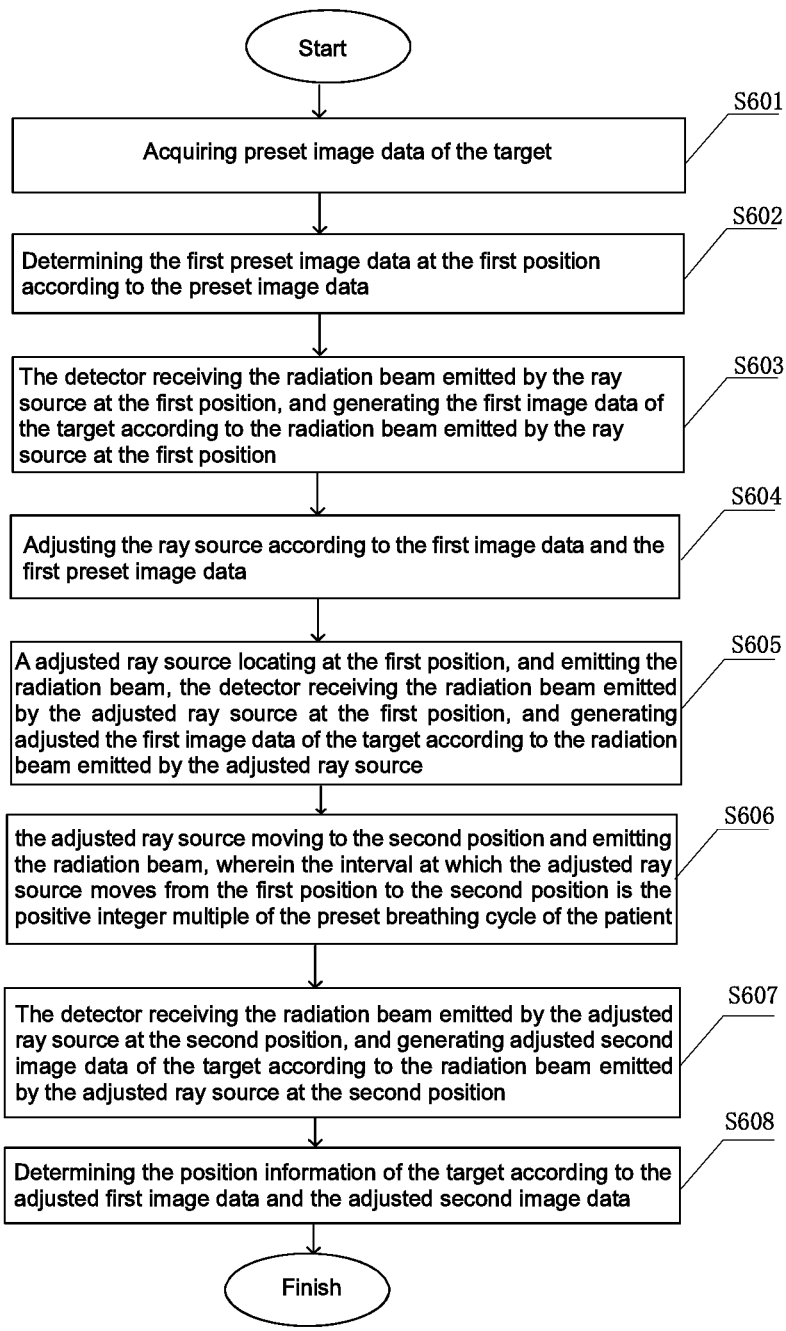
FIG. 11 is a flow diagram of yet still another method for determining target positions using a radiotherapy apparatus according to some embodiments of the present disclosure.

Exemplary, as shown in FIG. 11, the method includes:

S601: acquiring preset image data of the target;

S602: determining the first preset image data at the first position according to the preset image data;

S603: the detector receiving the radiation beam emitted by the ray source at the first position, and generating the first image data of the target according to the radiation beam emitted by the ray source at the first position;

S604: adjusting the ray source according to the first image data and the first preset image data;

S605: an adjusted ray source locating at the first position, and emitting a radiation beam, the detector receiving the radiation beam emitted by the adjusted ray source at the first position, and generating adjusted first image data of the target according to the radiation beam emitted by the adjusted ray source at the first position;

S606: the adjusted ray source moving to the second position and emitting a radiation beam, wherein the interval at which the adjusted ray source moves from the first position to the second position is the positive integer multiple of the preset breathing cycle of the patient;

S607: the detector receiving the radiation beam emitted by the adjusted ray source at the second position, and generating adjusted second image data of the target according to the radiation beam emitted by the adjusted ray source at the second position;

S608: determining the position information of the target according to the adjusted first image data and the adjusted second image data.

Wherein, the preset image data of the target acquired may be image data of the target acquired through CT, nuclear magnetic resonance, or B-ultrasound and the like during the time of diagnosis of the patient, and also may be image data of the target acquired by fusing the image data acquired by the above different methods. During treating the patient, the image data acquired in the above S601 to S608 are compared with the image data (i.e., the preset image data) when the doctor performs a treatment plan, so that the correctness of the treatment plan can be further confirmed. In addition, according to the comparison between the first image data and the first preset image data, the change situation of the target is acquired, so that the treatment plan or a range, an angle and the like of the radiation beam of the ray source in the treatment plan can be adjusted to achieve more accurate radiation therapy. Of course, a treatment source may be the ray source or different from the ray source, and the above contents take the treatment source being the ray source as an example. When the treatment source is different from the ray source, S604 may also specifically be to adjust the treatment source.

Of course, the ray source may also be adjusted according to the second image data and a second preset image data in the above embodiments, the method of which is similar to the above method, which will not be repeated herein again. Of course, the ray source may also be adjusted by comparing both the first image data with the first preset image data, and the second image data with the second preset image data.

Some embodiments of the present disclosure provide a device corresponding to the above method. The functions of some devices can be referred to the description in the above method, which will not be repeated herein again.

Figure 12:
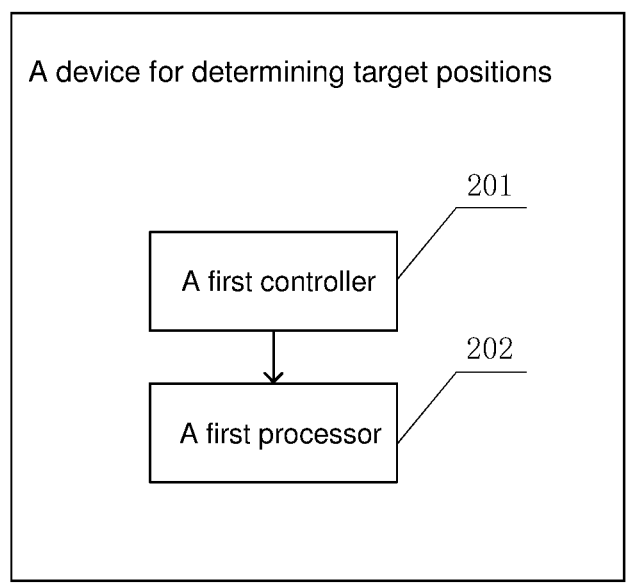
FIG. 12 is a schematic diagram of a device for determining target positions using a radiotherapy apparatus according to some embodiments of the present disclosure.

As shown in FIG. 12, the embodiments of the present disclosure disclose a device for determining target positions using a radiotherapy apparatus. The radiotherapy apparatus includes a ray source and a detector receiving rays emitted by the ray source, and the device includes:

a first controller 201, which is configured to: control the ray source to locate at a first position, and to emit a radiation beam; control the detector to receive the radiation beam emitted by the ray source at the first position, and to generate first image data of the target according to the radiation beam emitted by the ray source at the first position. And the first controller 201 is further configured to: control the ray source to move to a second position, and to emit a radiation beam; control the detector to receive the radiation beam emitted by the ray source at the second position, and to generate second image data of the target according to the radiation beam emitted by the ray source at the second position, wherein an interval at which the ray source moves from the first position to the second position is a positive integer multiple of a preset breathing cycle of a patient;

a first processor 202, which is configured to determine position information of the target according to the first image data and the second image data.

In this way, the detector receives the radiation beam emitted by the ray source at the first position and generates the first image data, and then the detector receives the radiation beam emitted by the ray source at the second position and generates the second image data. Since the interval at which the ray source moves from the first position to the second position is the positive integer multiple of the breathing cycle of the patient, the first image data and second image data that are acquired are image data of the same node in different breathing cycles of the patient, thereby avoiding the problem of inaccurate tumor imaging caused by time delay, and then providing more accurate position information of the target for radiotherapy, and avoiding damage caused by additional irradiation to normal organs around the target during radiotherapy.

Some embodiments of the present disclosure provide the device for determining target positions using the radiotherapy apparatus. As shown in FIG. 5, the device includes: the first controller 201, which is configured to: control the ray source 1 to locate at the first position 11, and to emit the radiation beam; control the detector 3 to receive the radiation beam emitted by the ray source 1 at the first position 11, and to generate the first image data of the target according to the radiation beam emitted by the ray source 1 at the first position 11. The first controller 201 is configured to: control the ray source 1 to move to a third position 13, and to emit a radiation beam; control the detector 3 to receive the radiation beam emitted by the ray source 1 at the third position 13, and to generate third image data of the target according to the radiation beam emitted by the ray source 1 at the third position 13. And the first controller 201 is further configured to: control the ray source 1 to move to the second position 12, and to emit the radiation beam; control the detector 3 to receive the radiation beam emitted by the ray source 1 at the second position 12, and to generate the second image data of the target according to the radiation beam emitted by the ray source 1 at the second position 12, wherein the interval at which the ray source moves from the first position to the second position is the positive integer multiple of the preset breathing cycle of the patient. The device further includes a second processor, which is configured to acquire motion trajectory information of the target in one preset breathing cycle according to the first image data, the third image data, and the second image data.

Exemplary, as shown in FIG. 6, the third position includes at least two different positions, such as a first third position 131 and a second third position 132 in FIG. 6. The third position may also include a plurality of different positions. The first controller 201 is configured to control the detector to generate at least two different third image data of the target respectively according to at least two different positions. The second processor 203 is further configured to acquire the motion trajectory information of the target in one preset breathing cycle according to the first image data, the second image data, and the at least two different third image data.

Some embodiments of the present disclosure provide the device for determining target positions using the radiotherapy apparatus. Exemplary, taking the device shown in FIG. 12 as an example, the device further includes: a fourth processor, which is configured to acquire a current breathing cycle of the patient, and adjust the preset breathing cycle according to the current breathing cycle.

The breathing cycle of the patient can be acquired through breathing training and the like before treatment, thereby acquiring the preset breathing cycle. When the patient is just starting treatment, the preset breathing cycle can be used to perform radiotherapy or imaging for the patient. In order to perform more precise treatment, the current breathing cycle of the patient can be acquired, so that it can be known whether the breathing cycle of the patient has changed. If a change has been occurred, the preset breathing cycle can be replaced with the current breathing cycle before the next breathing cycle starts.

In some embodiments of the present disclosure, the device further includes:

a third processor, which is configured to acquire the current breathing cycle of the target according to the first image data, the second image data, and the third image data, and then adjust the preset breathing cycle according to the current breathing cycle.

That is, by collecting image data of the target, the motion trajectory of the target is acquired according to the image data, and the breathing cycle is acquired according to the motion trajectory. The breathing cycle obtained by using this method is more precise in the breathing tracking. As described above, in this embodiment, the current breathing cycle of the patient can be acquired by using this method, so that it can be known whether the breathing cycle of the patient has changed. If a change has been occurred, the preset breathing cycle is replaced with the current breathing cycle of the patient acquired, so that the breathing cycle is more accurate, thereby providing more accurate data for treatment. The method adopted in the embodiment can quickly acquire the current breathing cycle of the patient, and is convenient for implementation and use in treatment.

Some embodiments of the present disclosure provide the device for determining target positions using the radiotherapy apparatus. Taking the device shown in FIG. 12 as an example, the device includes:

a fifth processor, which is configured to acquire at least one breathing node of the preset breathing cycle.

In this method, the ray source can be controlled to emit a radiation beam at a preset breathing node, and after receiving the radiation beam, the detector acquires image data, which can be compared with image data of other identical breathing nodes. In this way, a current state of the patient can be compared with a previous state at the same node to determine whether the breathing cycle of the patient has changed, and a specific value of breathing cycle change is specifically determined by a magnitude of the position change, thereby acquiring the current breathing cycle of the patient. The preset breathing cycle can also be replaced with the current breathing cycle of the patient acquired after acquiring the current breathing cycle of the patient, so that the breathing cycle is more accurate, thereby providing more accurate data for treatment.

Some embodiments of the present disclosure provide the device for determining target positions using the radiotherapy apparatus, and the device includes:

a sixth processor, which is configured to acquire image data of the same breathing node in different breathing cycles, determining the current breathing cycle of the patient according to the image data of the same breathing node in different breathing cycles, and adjust the preset breathing cycle according to the current breathing cycle.

Exemplary, taking the device shown in FIG. 12 as an example, wherein taking the first position being an inhalation node as an example, the device includes:

the first controller 201, wherein at the inhalation node of a first breathing cycle, the first controller 201 is configured to: control the ray source to locate at the first position at the inhalation node of a first breathing cycle, and to emit a radiation beam; control the detector to receive the radiation beam emitted by the ray source at the first position, and to generate first image data of the target in the first breathing cycle according to the radiation beam emitted by the ray source at the first position. At an exhalation termination node of the first breathing cycle, the first controller 201 is further configured to: control the ray source to move to the second position, and to emit a radiation beam, wherein an interval at which the ray source moves from the first position to the second position is the positive integer multiple of the preset breathing cycle of the patient; control the detector to receive the radiation beam emitted by the ray source at the second position, and to generate second image data of the target in the first breathing cycle according to the radiation beam emitted by the ray source at the second position;

at an inhalation node of a second breathing cycle, the first controller 201 is configured to: control the ray source to locate at the first position, and to emit a radiation beam; control the detector to receive the radiation beam emitted by the ray source at the first position, and to generate first image data of the target in the second breathing cycle according to the radiation beam emitted by the ray source at the first position. At an exhalation termination node of the second breathing cycle, the first controller 201 is further configured to control the ray source to move to the second position, and to emit a radiation beam, wherein the interval at which the ray source moves from the first position to the second position is the positive integer multiple of the preset breathing cycle of the patient; control the detector to receive the radiation beam emitted by the ray source at the second position, and to generate second image data of the target in the second breathing cycle according to the radiation beam emitted by the ray source at the second position;

the first processor 202, which is configured to: determine position information of the target in the first breathing cycle according to the first image data in the first breathing cycle and the second image data in the first breathing cycle; determine position information of the target in the second breathing cycle according to the first image data in the second breathing cycle and the second image data in the second breathing cycle; and determine the current breathing cycle of the patient according to the first image data in the first breathing cycle and the first image data in the second breathing cycle.

Of course, the first processor 202 may also be configured to determine the current breathing cycle of the patient according to the second image data in the first breathing cycle and the second image data in the second breathing cycle.

In this way, through comparing the image data acquired from the same breathing node in different breathing cycles in the treatment process, the image data of the same breathing node in different breathing cycles can be compared with each other to determine whether the breathing cycle of the patient has changed, and a magnitude of the change is acquired through the image data.

Through this method of the embodiment, through comparing the image data of the same breathing node in different breathing cycles in the treatment process, a change state of the breathing cycle can be acquired and the value of the current breathing cycle of the patient can be acquired, so that the preset breathing cycle is adjusted according to the current breathing cycle acquired, thereby providing more accurate data for treatment. In this way, in the absence of the preset image data, the data of the current breathing cycle of the patient can be acquired by comparing the plurality of image data in the treatment, which is more convenient for acquiring the breathing cycle in the treatment.

Some embodiments of the present disclosure provide the device for determining target positions using the radiotherapy apparatus, the device further includes:

a seventh processor, which is configured to: acquire preset image data of the target, determine first preset image data at the first position according to the preset image data, and adjust the ray source according to the first image data and the first preset image data.

Wherein, the preset image data of the target acquired may be image data of the target acquired through CT, nuclear magnetic resonance, or B-ultrasound and the like during the time of diagnosis of the patient, or may be image data of the target acquired by fusing the image data acquired through the above different methods. The above device can compare the image data acquired in the treatment process with the image data (i.e., the preset image data) when the doctor performs a treatment plan, so that the correctness of the treatment plan can be further confirmed. And according to a comparison between the first image data and the first preset image data, the change situation of the target is acquired, so that the treatment plan or a range, an angle and the like of the radiation beam of the ray source in the treatment plan can be adjusted to achieve more accurate radiation therapy.

Some embodiments of the present disclosure further disclose a radiotherapy apparatus. The radiotherapy apparatus includes a ray source and a detector receiving rays emitted by the ray source, and further includes any device described above for determining target positions using a radiotherapy apparatus.

The radiotherapy apparatus provided by the embodiments of the present disclosure may be an accelerator, a gamma knife, or a combination device of an accelerator and a gamma knife, etc. A specific type of the radiotherapy apparatus is not limited in the present disclosure.

The above contents are further detailed description for the present disclosure in combination with the specific preferred embodiments, but the specific embodiments of the present disclosure are not limited to the description. For a person of ordinary skill in the art to which the present disclosure pertains, some simple deductions or replacements may still be made without departing from the concept of the present disclosure, which shall all be considered as belonging to the protection scope of the present disclosure.

What is claimed is:

1. A method for determining target positions using a radiotherapy apparatus comprising:
   a ray source locating at a first position, and emitting a radiation beam;
   a detector receiving the radiation beam emitted by the ray source at the first position, and generating first image data of a target according to the radiation beam emitted by the ray source at the first position;
   the ray source moving to a second position, and emitting a radiation beam, wherein an interval at which the ray source moves from the first position to the second position is a positive integer multiple of a preset breathing cycle of a patient, the preset breathing cycle is a breathing cycle set by an initial input;
   the detector receiving the radiation beam emitted by the ray source at the second position, and generating second image data of the target according to the radiation beam emitted by the ray source at the second position; and
   determining position information of the target according to the first image data and the second image data;
   wherein before the ray source moves to the second position, the method further comprises:
   the ray source moving to a third position, and emitting a radiation beam;
   the detector receiving the radiation beam emitted by the ray source at the third position, and generating third image data of the target according to the radiation beam emitted by the ray source at the third position; and
   acquiring motion trajectory information of the target in the preset breathing cycle according to the first image data, the second image data, and the third image data.

2. The method according to claim 1, wherein the third position comprises at least two different positions, and the detector generates at least two third image data of the target at the at least two different positions respectively; and the motion trajectory information of the target in the preset breathing cycle is acquired according to the first image data, the second image data, and the at least two third image data.

3. The method according to claim 2 further comprising:
   acquiring a current breathing cycle of the target according to the first image data, the second image data, and the at least two third image data; and
   adjusting the preset breathing cycle according to the current breathing cycle.

4. The method according to claim 1 further comprising:
   acquiring a current breathing cycle of the patient according to the first image data and the second image data; and
   adjusting the preset breathing cycle according to the current breathing cycle.

5. The method according to claim 1 further comprising:
   setting at least one breathing node of the preset breathing cycle; and
   the ray source locating at the first position, and emitting a radiation beam at one of the at least one breathing node.

6. The method according to claim 5 further comprising:
   acquiring image data of a same breathing node in different preset breathing cycles;
   determining a current breathing cycle according to the image data of the same breathing node in the different preset breathing cycles; and
   adjusting the preset breathing cycle according to the current breathing cycle.

7. The method according to claim 1, wherein the ray source is able to be rotated circumferentially around the patient, and an angle between the first position and the second position is 0°-180°.

8. The method according to claim 7 further comprising:
   setting a rotation rate of the ray source;
   wherein the rotation rate of the ray source is: $x=(\alpha/NT)$, wherein x is a rotational angular rate, $\alpha$ is the angle between the first position and the second position, T is the preset breathing cycle of the patient, and NT is the interval at which the ray source moves from the first position to the second position, and N is a positive integer.

9. The method according to claim 1 further comprising:
   acquiring preset image data of the target;
   determining first preset image data at the first position according to the preset image data;
   adjusting the ray source according to the first image data and the first preset image data; or/and
   acquiring preset image data of the target;
   determining second preset image data at the second position according to the preset image data; and
   adjusting the ray source according to the second image data and the second preset image data.

10. A radiotherapy apparatus, the radiotherapy apparatus comprising a computer device, a ray source and a detector receiving radiation beams emitted by the ray source, wherein the computer device is configured to:
    control the ray source to locate at a first position, and to emit a radiation beam;

control the detector to receive the radiation beam emitted by the ray source at the first position, and to generate first image data of a target according to the radiation beam emitted by the ray source at the first position;

control the ray source to move to a second position, and to emit a radiation beam;

control the detector to receive the radiation beam emitted by the ray source at the second position, and to generate second image data of the target according to the radiation beam emitted by the ray source at the second position; and determine position information of the target according to the first image data and the second image data generated by a first controller;

wherein an interval at which the ray source moves from the first position to the second position is a positive integer multiple of a preset breathing cycle of a patient, the preset breathing cycle is a breathing cycle set by an initial input; and/or an interval between the detector generating the first image data and the second image data is a positive integer multiple of a preset breathing cycle of a patient;

wherein the computer device is further configured to:

control the ray source to move to a third position, and to emit a radiation beam;

control the detector to receive the radiation beam emitted by the ray source at the third position, and to generate third image data of the target according to the radiation beam emitted by the ray source at the third position; and acquire motion trajectory information of the target in the preset breathing cycle according to the first image data, the third image data, and the second image data.

11. The radiotherapy apparatus according to claim 10, wherein the third position comprises at least two different positions, and the computer device is further configured to:

control the ray source to move to the at least two different positions;

control the detector to generate at least two different third image data of the target at the at least two different positions respectively; and acquire the motion trajectory information of the target in the preset breathing cycle according to the first image data, the second image data, and the at least two different third image data.

12. The radiotherapy apparatus according to claim 11, wherein the computer device is further configured to:

acquire a current breathing cycle of the target according to the first image data, the second image data, and the at least two different third image data; and adjust the preset breathing cycle according to the current breathing cycle.

13. The radiotherapy apparatus according to claim 10, wherein the computer device is further configured to:

acquire a current breathing cycle of the patient; and adjust the preset breathing cycle according to the current breathing cycle.

14. The radiotherapy apparatus according to claim 10, wherein the computer device is further configured to:

acquire at least one breathing node of the preset breathing cycle.

15. The radiotherapy apparatus according to claim 13, wherein the computer device is further configured to:

acquire image data of a same breathing node in different preset breathing cycles;

determine the current breathing cycle of the patient according to the image data of the same breathing node in the different preset breathing cycles; and adjust the preset breathing cycle according to the current breathing cycle.

16. The radiotherapy apparatus according to claim 10, wherein the ray source is able to be rotated circumferentially around the patient, the computer device is further configured to:

control a rotation of the ray source, wherein, a rotation rate of the ray source is: $x=(\alpha/NT)$, wherein x is a rotational angular rate, $\alpha$ is an angle between the first position and the second position, T is the preset breathing cycle of the patient, and NT is the interval at which the ray source moves from the first position to the second position, and N is a positive integer.

17. The radiotherapy apparatus according to claim 10, wherein the computer device is further configured to:

acquire preset image data of the target, determine first preset image data at the first position according to the preset image data, and adjust the ray source according to the first image data and the first preset image data; or/and acquire preset image data of the target, determine second preset image data at the second position according to the preset image data, and adjust the ray source according to the second image data and the second preset image data.

* * * * *